(12) United States Patent
Dillon

(10) Patent No.: US 6,581,627 B2
(45) Date of Patent: Jun. 24, 2003

(54) DIALYSIS WALL STATION

(76) Inventor: Jack R. Dillon, 14303 W. 99th St., Shawnee Mission, KS (US) 66215

( * ) Notice: Subject to any disclaimer, the term of this patent is extended or adjusted under 35 U.S.C. 154(b) by 0 days.

(21) Appl. No.: 09/896,615

(22) Filed: Jun. 29, 2001

(65) Prior Publication Data

US 2002/0000402 A1 Jan. 3, 2002

Related U.S. Application Data

(60) Provisional application No. 60/215,271, filed on Jun. 30, 2000.

(51) Int. Cl.[7] .............................................. A47B 77/06
(52) U.S. Cl. ....................................... 137/360; 312/229
(58) Field of Search ........................... 137/360; 312/229

(56) References Cited

U.S. PATENT DOCUMENTS

| | | |
|---|---|---|
| 3,148,698 A | 9/1964 | Arnold |
| 3,495,276 A * | 2/1970 | Suess ......................... 137/360 |
| 3,834,781 A | 9/1974 | Logsdon |
| 4,158,471 A | 6/1979 | Logsdon |
| 4,646,211 A * | 2/1987 | Gallant et al. .............. 362/149 |
| 4,804,012 A * | 2/1989 | Goldman et al. ........... 137/343 |
| 5,538,033 A * | 7/1996 | Condon ....................... 137/360 |
| 5,560,231 A * | 10/1996 | Hwang ......................... 68/207 |

OTHER PUBLICATIONS

Dillon, Jack, Typical Cabinet Chase, Feb. 19, 1993, one (1) page, U. S. A.
Dillon, Jack, Small Whith Recessed Water and Concentrate Wall Box, one (1) page, U. S. A. 2000.
Great Water Company, Inc., Dialysis Patient Wall Stations, one (1) page, U. S. A. 2000.
Great Water Company, Inc., New Dialysis Patient Wall Station is First to Offer User–Friendly Features, 2000.
Great Water Company, Inc., Medical Solutions Divisions Newsletter, pp. 1 and 3, U. S. A. 2000.

* cited by examiner

Primary Examiner—A. Michael Chambers
(74) Attorney, Agent, or Firm—Chase Law Firm, L.C.

(57) ABSTRACT

A dialysis wall station is disclosed which presents a recessed solutions distribution area having a valve panel, an intermediate cantilevered connections panel and drain area. The drain area includes a back wall, an inclined floor that extends downwardly to a rear corner drain and a front lip. The wall station also includes a valve clamping block for securely mounting the solution valves to the wall station.

15 Claims, 2 Drawing Sheets

DIALYSIS WALL STATION

This Appln claims benefit of Prov. No. 60/215,271 filed Jun. 30, 2000.

FIELD OF THE INVENTION

This invention relates to a dialysis wall station having a drain and a recessed solution distribution center which includes a valve panel and a cantilever style connections panel for easy, efficient and safe dispensing of the dialysis solutions and water.

BACKGROUND OF THE INVENTION

Hemodialysis is a critical care medical technique which sustains the lives of thousands of patients who suffer from acute or chronic kidney failure. Ease of administration by healthcare professionals before, during and after the procedure helps to reduce the procedure's inherent complexity and avoidable adverse patient events.

SUMMARY OF THE INVENTION

Accordingly, a primary object of the subject invention is to provide a dialysis wall station that includes a recessed solution distribution center having a valve panel and a cantilevered connections panel.

Another important object of the subject invention is to provide a dialysis wall station having a sink basin that extends angularly downwardly to a corner drain.

Still another object of the subject invention is to provide a dialysis wall station that offers new freedom for dialysis staff because it does not project into the treatment area, and is easy to install, operate and clean.

Yet another object of the subject invention is to provide a dialysis wall station that is very durable.

Yet another object of the subject invention is to provide a dialysis wall station that protects valve handles from accidental damage.

Yet a further object of the subject invention is to provide a dialysis wall station that can be retrofit into an existing facility.

Yet a further object of the subject invention is to provide a dialysis wall station that accommodates compatible rinse ports from any dialysis delivery system with easy installation of valves, fittings, pressure gauges and quick connects.

Still another object of the subject invention is to provide a dialysis wall station having a recessed configuration that greatly reduces spills and stains, and protects fittings from damage by movement of equipment in the treatment area.

DETAILED DESCRIPTION

Figure 1:
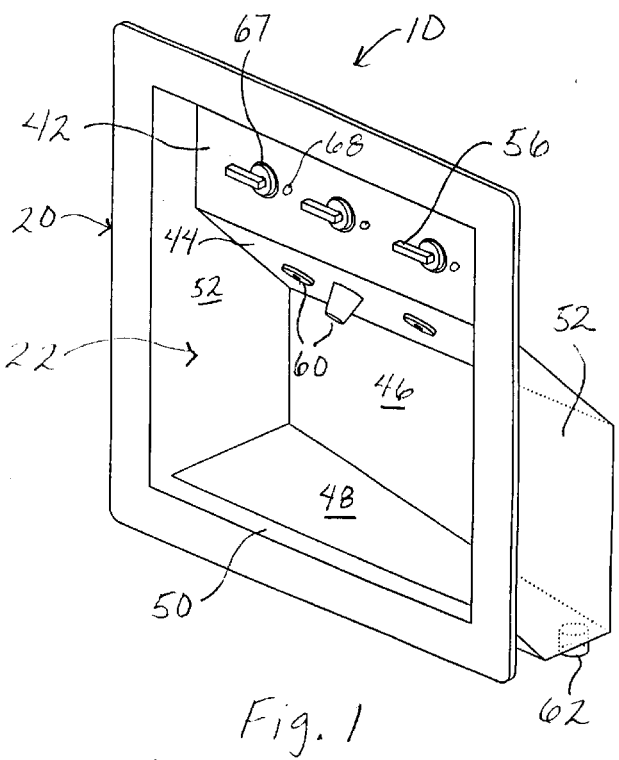
FIG. 1 is a perspective view of a dialysis wall station in accordance with the present invention.
Figure 4:
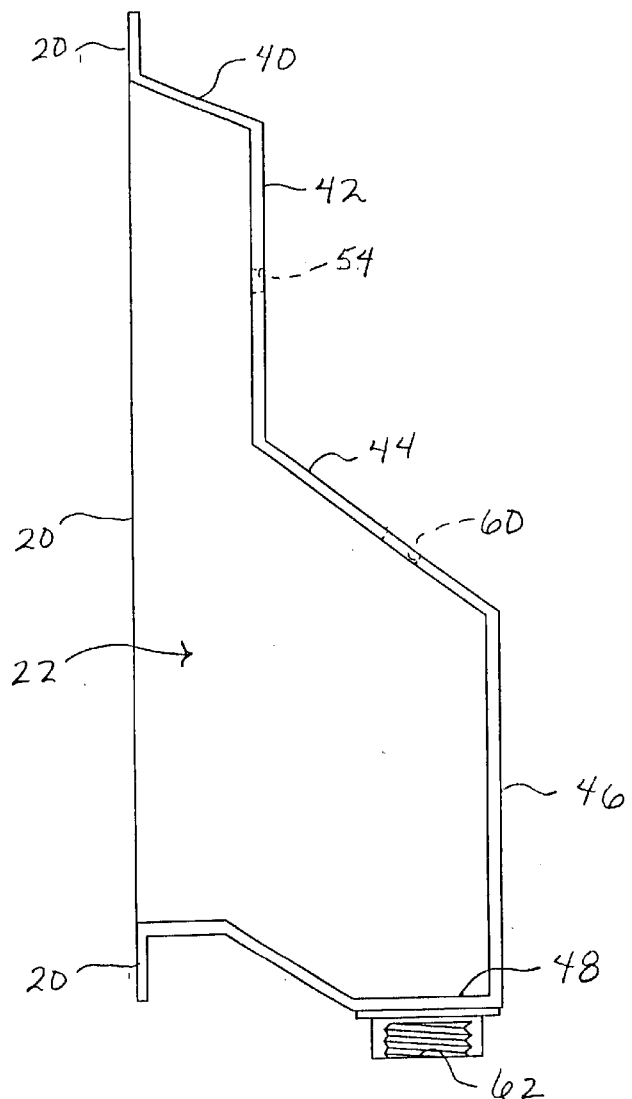
FIG. 4 is an enlarged vertical section along line 3—3 of FIG. 2 of the dialysis station, parts being removed for clarity.

Recessed dialysis wall station 10, as shown in FIG. 1, is for dispensing fluids such as bicarbonated and multiple acidified solution and RO/DI water, used during the hemodialysis process. The wall station 10 is easily mountable in a square wall opening, preferably 15 inches by 15 inches (38 cm.), for newly installed dialysis systems or for retrofitting with existing systems. The wall station 10 is formed from one piece of rigid, molded plastic, preferably polyethylene, which is durable and is stain resistant for ease of cleaning. The wall station 10 includes perimeter frame or flange 20, solutions distribution area 22 and valve clamping block 24.

Figure 2:
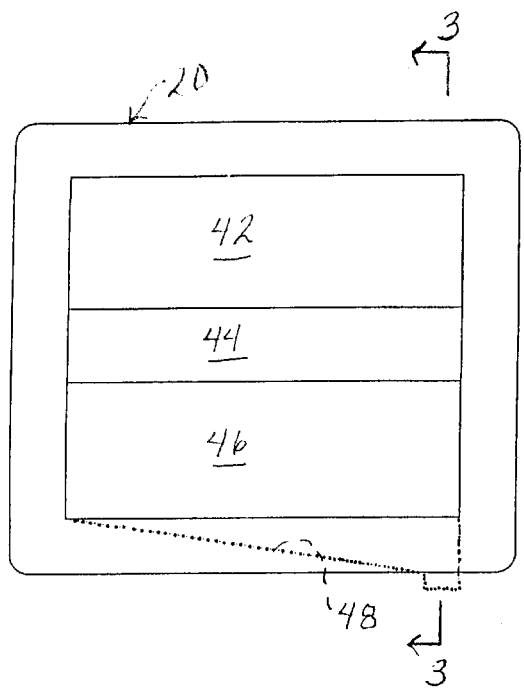
FIG. 2 is a front elevation view of the dialysis station of FIG. 1 with the valve components removed.
Figure 3:
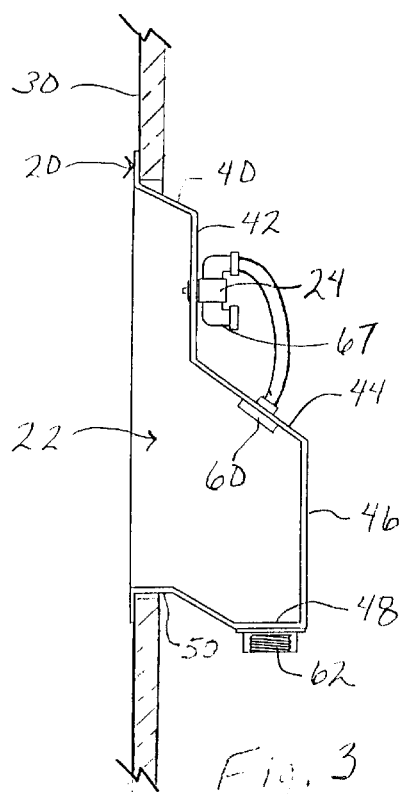
FIG. 3 is a slightly reduced vertical section along line 3—3 of FIG. 2 showing the dialysis station of FIG. 1 mounted in an interior wall.

In a treatment room or area, the wall station 10 is mounted flush with an interior wall 30 along flange 20, the rear surface of which abuts the interior wall surface as shown in FIG. 3. Preferably, flange 20 is approximately 2½ inches (6.3 cm.) wide. Flange 20 may be secured to the wall surface in any conventional manner.

The solutions distribution area 22 is defined by a plurality of walls, including a top wall 40, valve panel 42, connections panel 44, rear drain wall 46, bottom drain floor 48, front drain lip 50 and sidewalls 52. The top wall 40 extends from the upper portion of flange 20 angularly inwardly and downwardly into communication with vertically extending intermediate valve panel 42. The valve panel 42 may be configured to accommodate any dialysis system but generally will include a plurality of horizontally spaced valve access openings 54 for mounting a conventional valve 67 in each opening 54. A handle 56 is mounted to each valve 67 for opening and closing the corresponding valve. As shown, the wall station 10 illustrated includes three valves 67 in a horizontal row.

The connections panel 44 meets with the valve panel 42 along its upper horizontal edge and the rear drain wall 46 at its lower horizontal edge and extends angularly rearwardly and downwardly therebetween to present a cantilevered surface. Distribution ports 60 extend through panel 44, and comprise dialysis machine specific quick disconnect end point connectors. The number of ports 60 (three shown) preferably corresponds to the number of valves 67. The recessed nature of the valve panel 42 and connections panel 44 protects the valve handles 56 and distribution ports 60 from damage and allows healthcare professionals freedom from interference with otherwise projecting components to the dialysis equipment during the treatment.

The rear drain wall 46 extends vertically downward from the connections panel 44 until it meets the bottom, substantially horizontally extending drain floor 48. The floor 48 inclines or is angled downwardly to drain opening 62, which is preferably located adjacent a back rear corner of the floor 48. The front drain lip 50 extends upwardly from the drain floor 48 to the bottom portion of the flange 20. The sidewalls 52 enclose the distribution area 22 and extend vertically between the floor 48 and top wall 40.

In use, the inclination of the drain floor 48 directs discharged solution into the drain opening 62. The rear drain wall 46, front drain lip 50 and sidewalls 52 confine any discharged solution within the distribution area 22 of the wall station 10 and prevent spillage into the treatment area adjacent the wall station 10. Also, any leakage after use and disconnection of the concentrate lines (not shown) drips into the drain.

Figure 5:
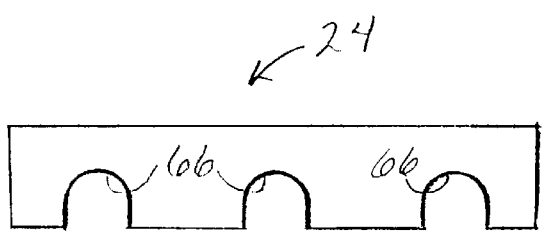
FIG. 5 is a plan detail view of the valve clamp of the dialysis wall station of FIG. 1.

As shown in detail in FIG. 5, the valve clamping block 24 is a rectangular saddle member formed of rigid plastic having arcuate cut-outs 66 formed in the front side thereof. Cut-outs 66 are shaped to receive and secure valves 67 to the rear surface of the valve panel 42. The clamping block 24 is held in place by three screws 68, but may be secured by any conventional means such as with adhesive.

What is claimed is:

1. A dialysis station for recessed mounting on a wall comprising:
   a mounting member adapted to engage a surface of the wall;
   a valve panel extending from said mounting member, said valve panel presenting a surface recessed from said mounting member;
   a connections panel extending from said valve panel and being further recessed from said mounting member; and
   a rear wall, a drain floor and a containment lip presenting a solution containment area formed below said connections panel, said lip projecting upwardly from said floor.

2. The dialysis station of claim 1 wherein said mounting member is a perimetrical flange.

3. The dialysis station of claim 1 wherein said valve panel presents a substantially vertical surface extending downwardly from said mounting member.

4. The dialysis station of claim 3 wherein said connections panel is inclined, extending angularly downwardly from said valve panel to a rear wall of said solution containment area.

5. The dialysis station of claim 1 further comprising:
   a valve clamping block including arcuate cut-outs formed in one side thereof and arranged in series, said cut-outs shaped to receive and secure valve members to a rear surface of said valve panel.

6. The dialysis station of claim 5 wherein said clamping block is elongated and substantially rectangular.

7. The dialysis station of claim 1 wherein
   said drain floor inclines downward to a lowest point of incline;
   a drain hole located at said lowest point of incline, whereby solutions spilled within said solution containment area are caused by gravity to flow down the incline of the drain floor and into said drain hole.

8. A dialysis station for recessed mounting on a wall comprising:
   a recessed solution distribution area including a valve access opening, a distribution port; and
   a recessed solution containment area including:
      a drain floor inclined downward to a lowest point of incline,
      a drain hole located at said lowest point of incline, and
      a containment member projecting upwardly from said floor to present said solution containment area, whereby solutions spilled within said solution containment area are caused by gravity to flow down the incline of the drain floor and into said drain hole.

9. The dialysis station of claim 8 wherein said containment member includes a front lip, sidewalls and a rear wall.

10. The dialysis station of claim 8 wherein said drain hole is located substantially adjacent a rear corner of said drain floor at said lowest point of incline.

11. The dialysis station of claim 8 wherein said valve access opening is formed in a recessed valve panel and said distribution port is formed in a further recessed connections panel that extends from said valve panel.

12. The dialysis station of claim 8 wherein said distribution port is formed in a recessed connections panel which presents a cantilevered surface extending between a recessed valve panel and a rear wall of said solution containment area.

13. A dialysis wall station for recessed mounting on a wall comprising:
   a recessed solution distribution area including a valve access opening and a distribution port;
   a recessed solution containment area below said solution distribution area;
   said containment area having a rear wall, a drain floor and a containment lip, said lip projecting upwardly from said floor; and
   a valve clamping block including arcuate cut-outs formed in one side thereof and arranged in series, said cut-outs shaped to receive and secure valve members to a rear surface of said solution distribution area adjacent said valve access opening.

14. The dialysis station of claim 13 wherein said valve access opening is formed in a recessed valve panel and said distribution port is formed in a further recessed connections panel that extends from said valve panel.

15. The dialysis station of claim 13 wherein said distribution port is formed in
   a recessed connections panel which presents a cantilevered surface extending between a recessed valve panel and a rear wall of said solution containment area.

* * * * *